(12) United States Patent
Hatch

(10) Patent No.: US 7,410,784 B2
(45) Date of Patent: Aug. 12, 2008

(54) QUANTITATION OF ENZYME ACTIVITY USING PLANAR WAVEGUIDES

(75) Inventor: Richard B. Hatch, Berkeley, CA (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 11/099,462

(22) Filed: Apr. 6, 2005

(65) Prior Publication Data

US 2006/0051830 A1 Mar. 9, 2006

Related U.S. Application Data

(60) Provisional application No. 60/608,043, filed on Sep. 8, 2004.

(51) Int. Cl.
*C12N 11/00* (2006.01)
(52) U.S. Cl. ...................................... 435/174
(58) Field of Classification Search .................. None
See application file for complete search history.

(56) References Cited

U.S. PATENT DOCUMENTS 6,771,376 B2    8/2004   Budach

FOREIGN PATENT DOCUMENTS

WO    WO 2004/042377    5/2004

OTHER PUBLICATIONS

Rowe et al. Anal. Chem. 1999;71:433-439.*
Weinberger et al., "Recent trends in protein biochip technology," *Pharmacogenomics*, 2000, 1(4):395-416.
Zhylyak et al., "Planar integrated optical waveguide used as a transducer to yield chemical information: detection of the activity of proteolytic enzymes e.g. serine-protease," *Optics and Lasers in Engineering*, 43 (2005) 603-617.
Bockemühl et al., "Troponin I point-of-care testing using planar waveguide technology," presented at the Eighth World Congress on Biosensors, May 24-26, 2004, Granada, Spain.
Rowe-Taitt et al., "Array biosensor for detection of biohazards," *Biosensors & Bioelectronics 14*, 785-94, 2000.

* cited by examiner

*Primary Examiner*—Jon P Weber
*Assistant Examiner*—Bin Shen
(74) *Attorney, Agent, or Firm*—Banner & Witcoff, Ltd.

(57) ABSTRACT

Enzyme activity sensors comprising a planar waveguide can be used for sensitive and quantitative measurement of enzyme activity. Such enzyme activity sensors are useful in a variety of settings, including clinical, commercial, and public health settings.

34 Claims, 6 Drawing Sheets

QUANTITATION OF ENZYME ACTIVITY USING PLANAR WAVEGUIDES

This application claims the benefit of and incorporates by reference provisional application Ser. No. 60/608,043 filed Sep. 8, 2004.

FIELD OF THE INVENTION

The invention relates to methods of quantitating enzyme activity.

DETAILED DESCRIPTION OF THE INVENTION

Figure 1:
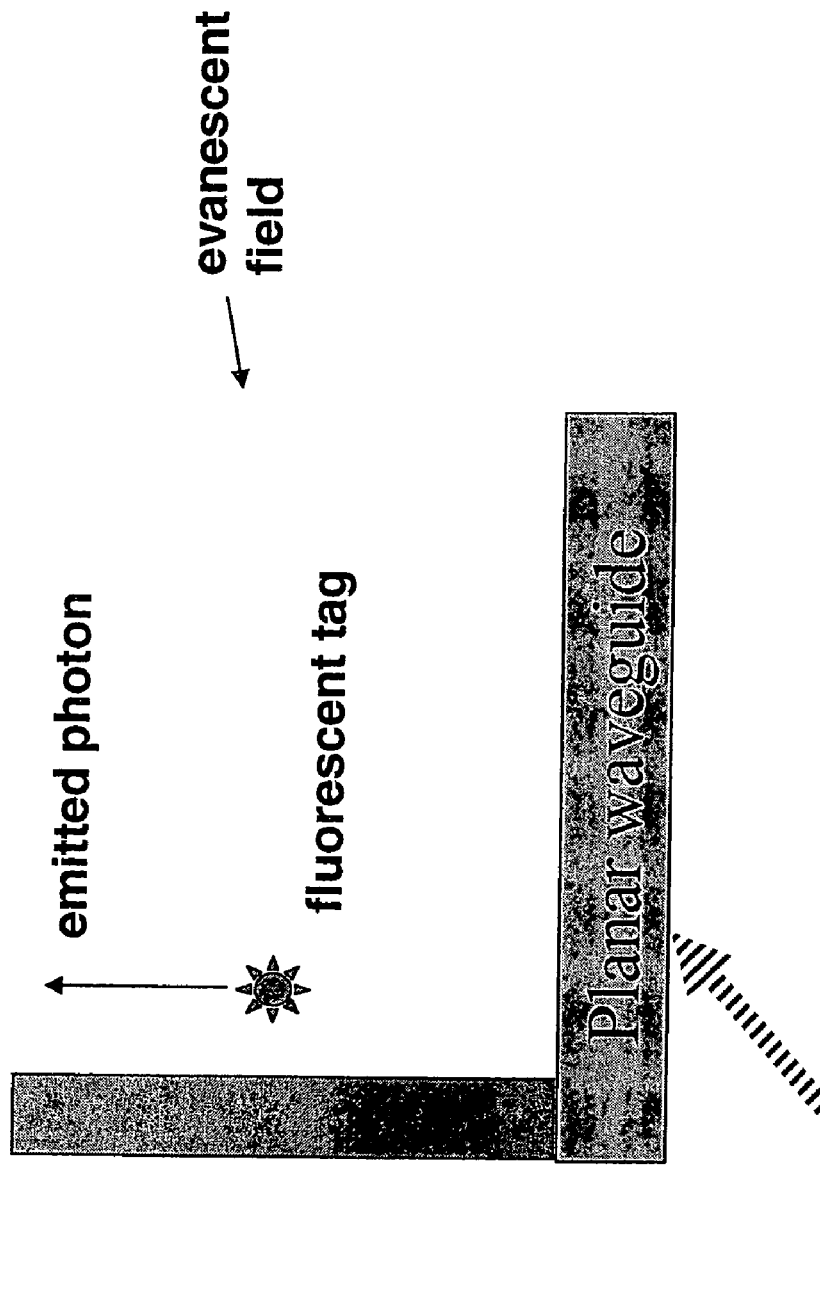
FIG. 1. Illustration of planar waveguide technology using a fluorescent tag.

The present invention provides enzyme activity sensors which employ planar waveguide technology for sensitive and quantitative measurement of enzyme activity. Enzyme activity sensors of the invention provide many advantages, including small scale of operation, speed, sensitivity, specificity, and ease of production. The sensors can be used in any environment in which measurement of enzyme activity is desired and can detect enzyme activity in complex fluid systems without sample purification. If desired, multiple enzyme assays can be conducted in parallel.

Planar Waveguides

Enzyme activity sensors of the invention comprise a planar waveguide which comprises one or more substrates for one or more enzymes. Planar waveguides typically contain a thin film of a material with a high refractive index (e.g., $Ta_2O_5$ or $TiO_2$) deposited on a transparent support with lower refractive index (e.g., glass or a polymer). Methods of making planar waveguide layers are well known in the art and any of the known methods can be used. See, e.g., U.S. Pat. No. 5,959,292; U.S. Pat. No. 6,078,705; U.S. Pat. No. 5,846,842; Rowe-Taitt et al., *Biosensors & Bioelectronics* 14, 785-94, 2000.

Immobilization of Enzyme Substrates on the Planar Waveguide

A substrate for the enzyme to be assayed is immobilized on the planar waveguide. Methods for immobilizing proteins are well known in the art and any such methods can be used to affix an enzyme substrate to a detection area. See, e.g., Scouten et al., *Trends in Biotechnology* 13, 178-85, 1995; Shriver-Lake et al., *Biosensors and Bioelectronics* 12, 1101-06, 1997; Rowe-Taitt et al., 2000. The method selected will depend to some extent on the nature of the particular enzyme substrate and is well within the skill of those in the art.

Typically, substrates are immobilized by covalent bonding directly on the planar waveguide layer or after chemical modification of the planar waveguide surface, for example by silanization or applying a polymer layer. If desired, a thin interlayer (e.g., $SiO_2$) can be applied directly to the planar waveguide layer to serve as an adhesion-promoting layer to facilitate the immobilization of an enzyme substrate on the waveguide.

In other embodiments, the planar waveguide layer is coated with avidin, and the enzyme substrates can be conjugated to a biotin moiety which has a very strong affinity for avidin. See Rowe-Taitt et al., 2000. In other embodiments, the waveguide is coated with a hydrogel film formed of polymethacryloyl-hydrazide which is treated to produce free maleimido groups; some enzyme substrates can be oxidized to produce reactive thiol groups which can then be reacted with the maleimido groups. In yet other embodiments, a silanized waveguide surface is coated with polyethylene glycol derivatized with ethylenediamine groups. These groups also can react with oxidized enzyme substrates.

Non-covalent interactions also can be used to affix a substrate to a planar waveguide. Such interactions include, but are not limited to, hydrophobic absorption, van der Waals interactions, hydrogen bonding, and electrostatic forces.

If a coating is used, it preferably is applied to the planar waveguide to achieve a reproducible, constant layer thickness. Typical examples methods which can be used to coat planar waveguides include spraying, knife-coating, spin-coating, or dip-coating. Quality control of the coatings can be carried out by any appropriate method, including microscopy, interferometry, ellipsometry, and measurements of contact angles.

Different enzyme substrates can be localized in different and mutually exclusive regions on the planar waveguide. The substrates preferably are arranged in a spatially addressable array. For example, multiple wells or channels can be provided on the surface of the waveguide to permit simultaneous comparison of detectable labels from control and sample solutions. Optionally, a substantial portion of the surrounding edge of the waveguide can be coated with a reflective coating to prevent light from escaping through the edge, which increases the intensity of the evanescent field. Spatially addressable arrays can also be prepared as regions or spots to allow the sensing of multiple enzyme activities within a single fluid sample.

Detectable Labels

In some of the embodiments described below the enzyme substrates comprises a detectable label. In other embodiments activity of the enzyme modifies the substrate to comprise a detectable label. Detectable labels for use in the invention typically are photoreactive labels, such as fluorescent labels, phosphorescent labels, and UV absorptive labels. Fluorescent labels are especially useful because excitation of the fluorophore by the field does not require trans-irradiation of the bulk fluid and thereby limits background signal, enhancing sensitivity. Methods of attaching detectable labels to polypeptides and other enzyme substrates are well known in the art.

Suitable labels include rhodamines, fluorescein derivatives, coumarin derivatives, distyryl biphenyls, stilbene derivatives, phthalocyanines, naphthalocyanines, polypyridyl-ruthenium complexes such as tris(2,2'-bipyridyl)-ruthenium chloride, tris(1,10-phenanthroline) ruthenium chloride, tris(4,7-diphenyl-1,10-phenanthroline) ruthenium chloride and polypyridyl-phenazine-ruthenium complexes, platinum-porphyrin complexes such as octaethyl-platinum-porphyrin, long-life europium and terbium complexes or cyanine dyes.

Dyes having absorption and emission wavelengths in the range from 600-900 nm are particularly suitable for analyses using blood or serum.

Particularly suitable detectable labels are dyes such as fluorescein derivatives which contain functional groups with which they can be covalently bound to a substrate, for example fluorescein isothiocyanate. Also very suitable are the functional fluorescent dyes available from Biological Detection Systems Inc., for example the mono- and bifunctional CY5.5™ dyes. *Clinical Chemistry* 40, 1819-22, 1994. If desired, substrates for different enzymes can comprise different detectable labels.

Examples of Enzyme Activity Sensors

Enzyme activity sensors of the invention can be used in several different "modes." Depending on which mode is used, the enzyme substrate may or may not comprise a detectable label as described above. Also depending on which mode is used, detection of enzyme activity can involve detecting either a decrease or an increase in the amount of detectable label.

Figure 2:
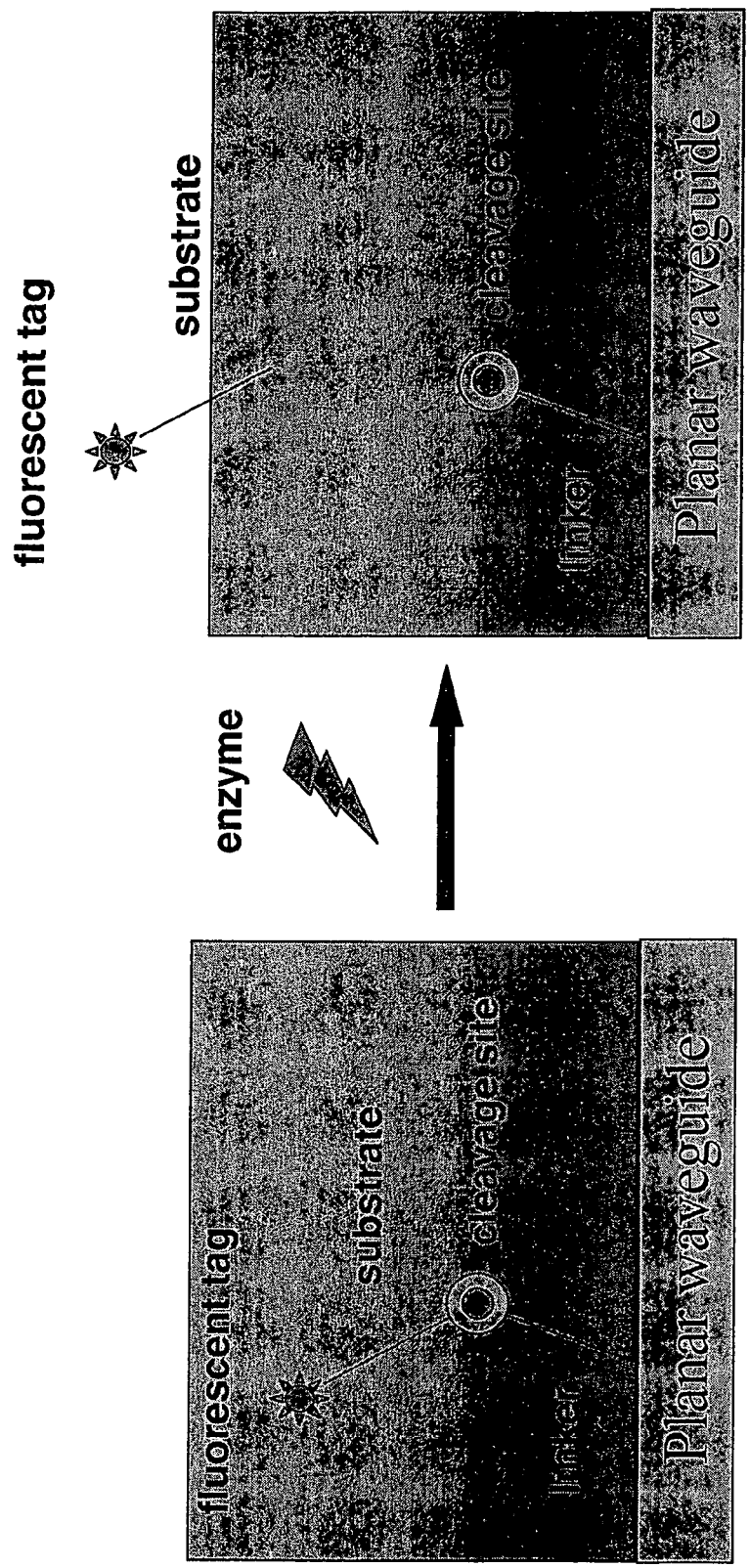
FIG. 2. Illustration of planar waveguide technology used in the "hydrolytic cleavage mode" with a fluorescent enzyme substrate.

For example, an enzyme activity sensor which comprises a detectably labeled substrate can be used in "hydrolytic cleavage mode." In this mode, the enzyme cleaves the substrate from the planar waveguide surface, and a decreased signal reflects enzyme activity. See FIG. 2.

Figure 3:
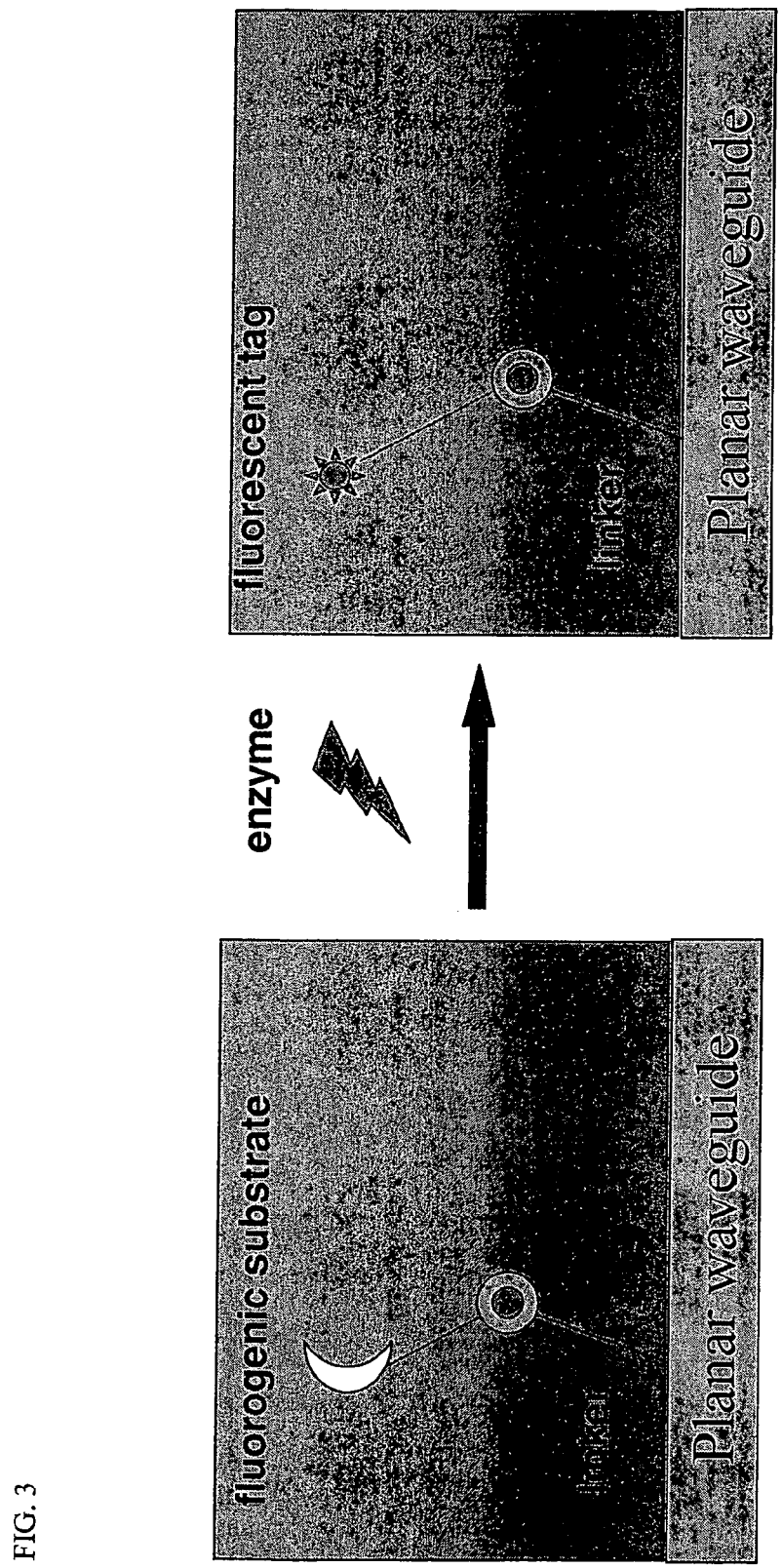
FIG. 3. Illustration of planar waveguide technology used in the "reactive transformation mode" using a fluorogenic enzyme substrate.

Other enzyme substrates comprises a moiety which an enzyme will modify into a detectable label or into a label which is no longer detectable ("reactive transformation mode"). If the enzyme modifies the moiety so that it generates a detectable label, enzyme activity will be reflected in an increased signal. On the other hand, if the enzyme modifies the moiety so that it no longer is detectable, a decreased signal reflects enzyme activity. See FIG. 3.

Figure 4:
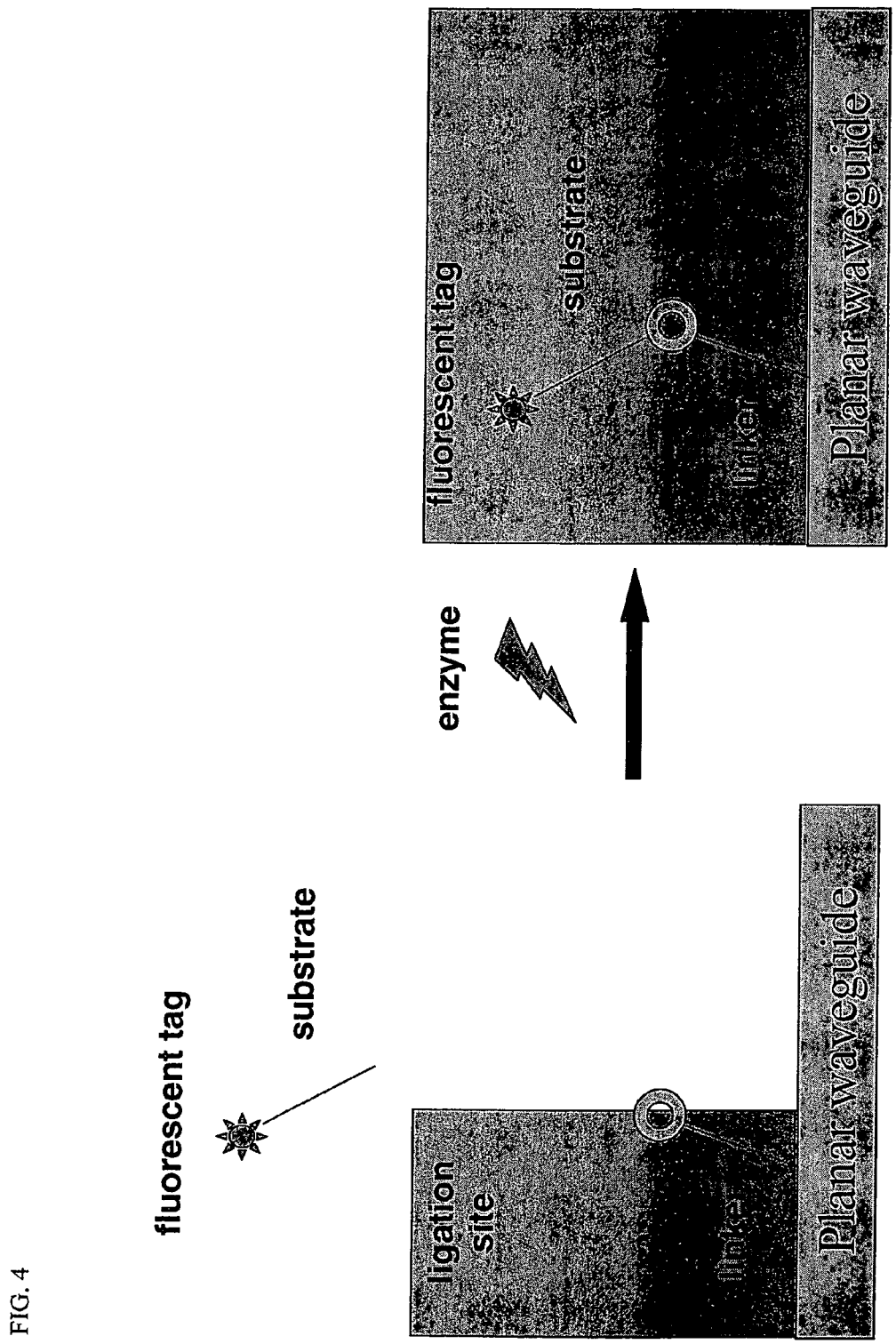
FIG. 4. Illustration of planar waveguide technology used in the "conjugation mode" using a fluorescent tag.

In still other embodiments the enzyme will conjugate a detectable label to the enzyme substrate ("conjugation mode"). See FIG. 4. In these embodiments an increased signal reflects enzyme activity.

Figure 5:
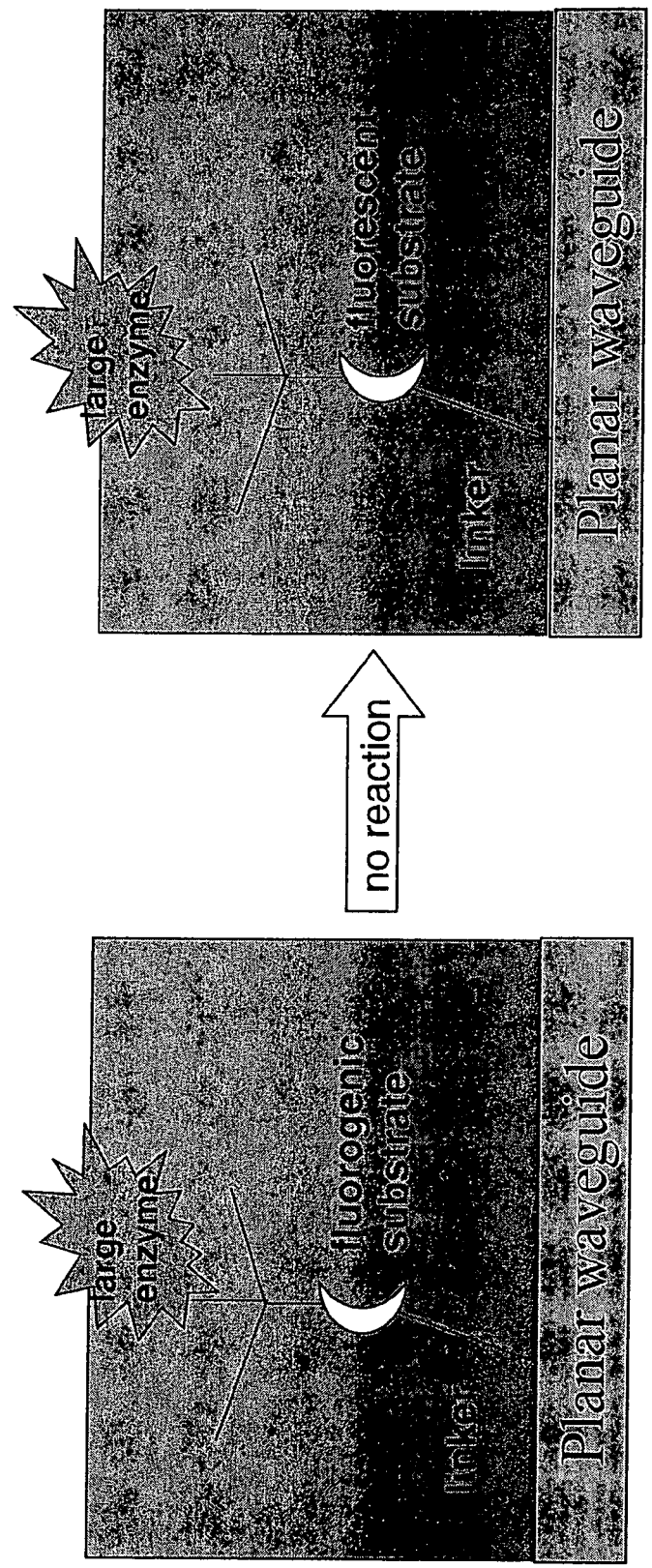
FIG. 5. Illustration of planar waveguide technology used in the "steric exclusion mode" using a fluorogenic enzyme substrate.

In some embodiments, substrate linkage or spacer structures can be used to increase selectivity for target enzyme activity by separating different enzyme substrates spatially, for example through steric, ionic, or hydrophobic interaction mechanisms ("steric exclusion mode"). See FIG. 5. These mechanisms are particularly useful in enzyme activity sensors of the invention, because the ability to spatially locate the labeled moiety of the detected molecules allows for controllable sensitivity of the detection process due to the exponential decay of the evanescent field intensity with distance from the planar waveguide sensor surface. Shriver-Lake et al., 1997.

For example, the use of different length spacers can permit balancing of fluorescent signals for different spots in a multiplexed assay. Similarly, since the site of enzymatic reaction can also be controlled by the same factors, the enhancement or elimination of certain specific reactions can be achieved in the presence of multiple potentially reactive molecules.

Figure 6:
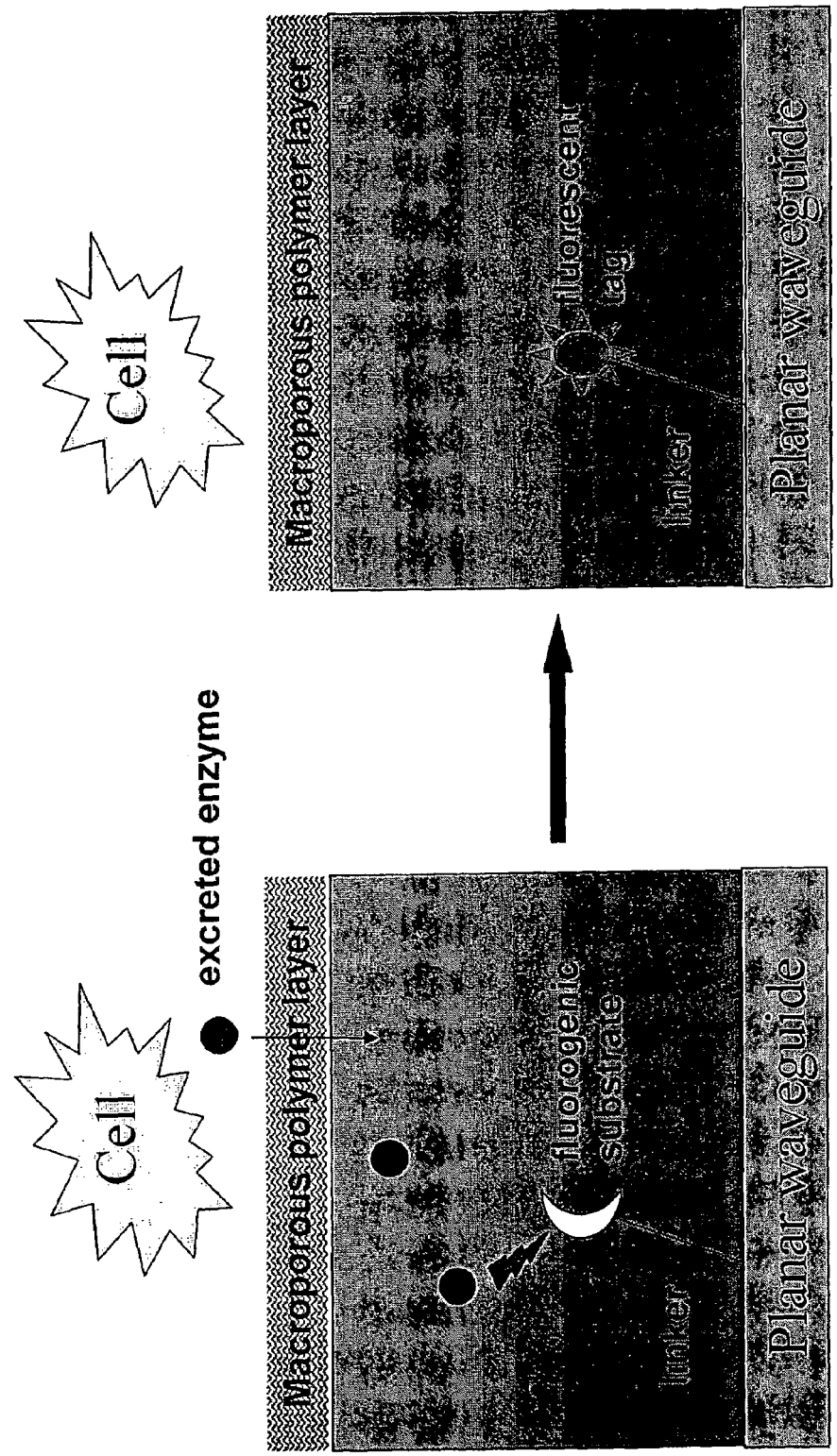
FIG. 6. Illustration of planar waveguide technology used in the "cellular isolation mode" using a fluorogenic enzyme substrate.

Any of the embodiments described above can be used in situ in a cell culture, to assay medium into which cells may excrete an enzyme ("cellular isolation mode"). See FIG. 6. In this case, the enzyme activity sensor can be separated from the cells, or from a single cell, by a macroporous polymer layer, such as a hydrophilic polymer (e.g., a polyhydroxylated methacrylate or a polysaccharide). The cellular isolation mode permits detection of enzymes secreted by living cells, under physiological conditions, without allowing contact between the cells and the substrate, or potential reaction products. Many enzyme activity detection systems are not compatible with living cells. This embodiment, therefore, is an improvement over prior art in that reaction systems can be used for detection that would be toxic or otherwise adversely affect the cells. The cellular isolation also allows measurement without potentially altering the cellular biology by irradiation.

Use of Enzyme Activity Sensors

The enzyme sensors disclosed herein can be used in any setting in which qualitative or quantitative assay of enzyme activity is desired. The activity of any type of enzyme can be detected, including, but not limited to, proteolytic enzymes (e.g., amino peptidase, aspartyl proteases, serine proteases, metallo proteases, cysteinyl proteases, pepsin, trypsin, thrombin, lysozyme, Factor VIII:C), glycosidases, esterases, hydrolases, nucleases, syntheases, isomerases, polymerases, kinases, phosphatases, reductases, including oxido-reductases, transferases, ligases, restriction enzymes, amidases, ATPases, carbohydrases, lipases, cellulases, dehydrogenases, and oxidases. Substrates for these enzymes are well known in the art and are widely available from commercial suppliers.

Enzyme activity sensors of the invention are particularly useful as diagnostic tools because they permit in situ, highly multiplexed real-time studies of complex biological enzyme systems. In particular, these sensors permit real-time monitoring of enzyme activity even in turbid fluids such as serum or blood without any sample preparation. The sensors can therefore easily be used as rapid diagnostic tools in a point of care environment.

In a clinical setting, the fluid which contacts the planar waveguide is of biological origin and includes, but is not limited to, blood, plasma, urine, cerebrospinal fluid, saliva, bronchial lavage fluid, aqueous humor, ascites fluid, extravascular lung water, follicular fluid, labyrinthine fluids, endolymph, perilymph, lymph, chyle, nasal lavage fluid, and synovial fluid. The fluid also can be medium in which cells of patient origin have been cultured.

Enzymes which are of clinical interest include, for example, amylase and lipase (pancreatic disease); creatinine kinase, lactate dehydrogenase, α-hydroxybutyrate dehydrogenase, serum glutamic oxaloacetic transaminase, and creatine phosphokinase (heart attacks, muscle disease, and strokes); amino alanine transferase, serum glutamic oxaloacetic transaminase, serum glutamic pyruvic transaminase, and lactate dehydrogenase (liver disease); alkaline phosphatase (liver or kidney disease); angiotensin converting enzyme (active sarcoidosis, atypical mycobacteria, primary biliary cirrhosis, Gaucher's disease, or leprosy); Factor VIII:C (hemophilia); renin (renovascular hypertension); galactose-1-phosphate uridyltransferase (galactosemia); glucocerebrosi-dase (Gaucher's disease); and biotinidase (biotinidase deficiency).

Enzyme activity sensors of the invention also can be used in a commercial or research setting, to monitor enzyme activity during large- or small-scale purification of an enzyme. They can be used to monitor enzyme activity in a fermentation medium. They can be used to detect public health hazards, for example to detect enzymes diagnostic of pathogenic bacteria, viruses, and fungi. Enzyme activity sensors of the invention also are useful in high throughput screening assays for therapeutic agents which can reduce a particular enzyme activity.

Generation and Detection of the Detectable Label

Enzyme activity sensors of the invention can sample a very small layer of a liquid for the detectable tag using the evanescent field generated by reflection of a beam of laser light inside the planar waveguide. The evanescent field extends about 100 nm into the liquid with an intensity that decays exponentially; thus, detectable tags which are outside the field are not detected. See FIG. 1.

A fluid which may comprise the enzyme to be assayed is placed in contact with the planar waveguide. The contact can be static or the fluid can be passed over the planar waveguide. Polarized light, most commonly from a laser source such as a small diode laser, is conducted by total reflectance to the interfaces of the waveguiding layer. An evanescent wave or field is generated by the internal reflectance of the light at the interface between materials of different refractive indices at the boundaries of the waveguide. The strength of the evanescent field depends on the thickness of the waveguiding layer itself as well as on the ratio of the refractive indices of the waveguiding layer and of the surrounding media. In the case of thin waveguides, i.e., layer thicknesses of the same or lesser thickness than of the wavelength to be guided, it is possible to distinguish discrete modes of the conducted light.

The evanescent field excites luminescence in the optically thinner medium of the planar waveguide, but only directly adjacent to the guided light wave. Methods and apparatus for detecting the evanescently excited luminescence are well known in the art and are described, for example, in U.S. Pat. No. 4,582,809; U.S. Pat. No. 5,081,012; WO 90/06503; and Biosensors & Bioelectronics 6 (1991), 595-607. Photodiodes, photocells, photomultipliers, CCD cameras and detector arrays, for example CCD cells, can be used. The luminescence can be imaged with optical elements such as mirrors, prisms, lenses, Fresnel lenses, and gradient index lenses. Known elements such as filters, prisms, monochromatic filters, dichromatic mirrors, and diffraction gratings can be used to select the appropriate emission wavelength.

All patents, patent applications, and references cited in this disclosure are expressly incorporated herein by reference in their entireties.

The invention claimed is:

1. An enzyme activity sensor comprising a planar waveguide which comprises a first substrate for a first enzyme and a second substrate for a second enzyme, wherein either:
   (1) the first substrate comprises a first detectable label and the second substrate comprises a second detectable label; or
   (2) activity of the first enzyme modifies the first substrate to comprise the first detectable label and activity of the second enzyme modifies the second substrate to comprise the second detectable label; and
   wherein the first substrate comprises a first spacer structure located between the surface of the planar waveguide and the first substrate and wherein the second substrate comprises a second spacer structure located between the surface of the planar waveguide and the second substrate, wherein the first spacer structure and the second spacer structure are of different lengths and permit balancing of detectable signals in a multiplexed assay.

2. The enzyme activity sensor of claim 1 further comprising a detection element.

3. The enzyme activity sensor of claim 1 wherein the first substrate comprises the first detectable label and wherein the second substrate comprises the second detectable label.

4. The enzyme activity sensor of claim 1 wherein the activity of the first enzyme modifies the first substrate to comprise the first detectable label and wherein the activity of the second enzyme modifies the second substrate to comprise the second detectable label.

5. The enzyme activity sensor of claim 3 wherein the first and the second detectable labels are selected from the group consisting of a fluorescent label, a phosphorescent label, and a UV absorptive label.

6. The enzyme activity sensor of claim 4 wherein the first detectable label is a fluorogenic moiety.

7. The enzyme activity sensor of claim 1 wherein the first enzyme is selected from the group consisting of an amidase, an esterase, an oxidase, a reductase, a polymerase, a transferase, a ligase, a restriction enzyme, and a protease.

8. The enzyme activity sensor of claim 1 wherein the first substrate and the second substrate are substrates for different enzymes.

9. The enzyme activity sensor of claim 1 wherein the first and second substrates are arranged in a spatially addressable array.

10. An enzyme activity sensor comprising a planar waveguide which comprises a substrate for an enzyme, wherein either:
    the substrate comprises a detectable label; or
    activity of the enzyme modifies the substrate to comprise the detectable label; and
    wherein the planar waveguide further comprises:
    a macroporous polymer layer which permits detection of enzyme activity in living cells.

11. The enzyme activity sensor of claim 10 wherein the macroporous polymer layer comprises a hydrophilic polymer.

12. The enzyme activity sensor of claim 11 wherein the hydrophilic polymer is selected from a group consisting of:
    a polyhydroxylated methacrylate; and
    a polysaceharide.

13. The enzyme activity sensor of claim 1 wherein the planar waveguide further comprises a macroporous polymer layer.

14. The enzyme activity sensor of claim 13 wherein the macroporous polymer layer comprises a hydrophilic polymer.

15. The enzyme activity sensor of claim 14 wherein the hydrophilic polymer is selected from a group consisting of:
    a polyhydroxylated methacrylate; and
    a polysaccharide.

16. An enzyme activity sensor comprising a planar waveguide which comprises a substrate for an enzyme, wherein either:
    the substrate comprises a detectable label; or
    activity of the enzyme modifies the substrate to comprise the detectable label; and
    wherein the substrate further comprises a spacer structure, wherein the spacer structure is located between the substrate and the enzyme.

17. The enzyme activity sensor of claim 16 wherein the substrate comprises a plurality of spacer structures.

18. The enzyme activity sensor of claim 16 wherein the spacer structure is charged.

19. The enzyme activity sensor of claim 16 wherein the spacer structure is hydrophobic.

20. The enzyme activity sensor of claim 16 wherein the spacer structure is branched.

21. A method of detecting enzyme activity, comprising steps of:
    (a) exposing the enzyme activity sensor of claim 1 to a test sample under conditions which permit the first enzyme to act upon the first substrate and which permit the second enzyme to act upon the second substrate;
    (a) irradiating the planar waveguide of the sensor to generate an evanescent field;
    (b) inspecting the evanescent field for the presence of detectable signals.

22. The method of claim 21, wherein the first substrate comprises the first detectable label.

23. The method of claim 22, wherein activity of the first enzyme releases the first detectable label from the first substrate.

24. The method of claim 22, wherein activity of the first enzyme reduces detectability of the first detectable label.

25. The method of claim 21, wherein activity of the first enzyme modifies the first substrate to comprise the first detectable label.

26. The method of claim 25, wherein the first enzyme conjugates the first detectable label to the first substrate.

27. The method of claim 25, wherein the first detectable label is a flurogenic moiety.

28. The method of claim 22, wherein the first detectable label is a photoreactive label.

29. The method of claim 28, wherein the photoreactive label is selected from the group consisting of a fluorescent label, a phosphorescent label, and a UV absorptive label.

30. The method of claim 29, wherein the first and second substrates are substrates for two different enzymes.

31. The method of claim 21, wherein the first and second substrates are arranged in a spatially addressable array.

32. The method of claim 21, wherein the test sample comprises a fluid selected from the group consisting of blood, plasma, urine, cerebrospinal fluid, saliva, bronchial lavage fluid, aqueous humor, ascites fluid, extravascular lung water, follicular fluid, labyrinthine fluids, endolymph, perilymph, lymph, chyle, nasal lavage fluid, synovial fluid, fermentation medium, and cell culture medium.

33. The method of claim 21, wherein step (b) comprises quantitative detection.

34. The method of claim 21, wherein step (b) comprises qualitative detection.

* * * * *

UNITED STATES PATENT AND TRADEMARK OFFICE
CERTIFICATE OF CORRECTION

PATENT NO. : 7,410,784 B2  Page 1 of 1
APPLICATION NO. : 11/099462
DATED : August 12, 2008
INVENTOR(S) : Richard G. Hatch It is certified that error appears in the above-identified patent and that said Letters Patent is hereby corrected as shown below:

Title page, Inventor (75):
  Please replace "Richard B. Hatch" with --Richard G. Hatch--

Signed and Sealed this

Twenty-third Day of June, 2009

JOHN DOLL
*Acting Director of the United States Patent and Trademark Office*